US009498186B2

(12) United States Patent
Kiyose et al.

(10) Patent No.: US 9,498,186 B2
(45) Date of Patent: Nov. 22, 2016

(54) LIVING BODY TESTING PROBE

(71) Applicant: SEIKO EPSON CORPORATION, Tokyo (JP)

(72) Inventors: Kanechika Kiyose, Nagano (JP); Daisuke Nakanishi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 41 days.

(21) Appl. No.: 13/708,051

(22) Filed: Dec. 7, 2012

(65) Prior Publication Data

US 2013/0150722 A1 Jun. 13, 2013

(30) Foreign Application Priority Data

Dec. 13, 2011 (JP) ................................. 2011-272131

(51) Int. Cl.
*A61B 8/14* (2006.01)
*A61B 8/00* (2006.01)

(52) U.S. Cl.
CPC ........... *A61B 8/4455* (2013.01); *A61B 8/4422* (2013.01); *A61B 8/4444* (2013.01); *A61B 8/462* (2013.01); *A61B 8/467* (2013.01)

(58) Field of Classification Search
CPC .................. A61B 8/4455; A61B 8/462; A61B 8/4422; A61B 8/4444; A61B 8/467
USPC ................................................. 600/437–480
See application file for complete search history.

(56) References Cited

U.S. PATENT DOCUMENTS

| 4,757,213 | A | * | 7/1988 | Tigges et al. ................. 307/116 |
| 5,722,412 | A | * | 3/1998 | Pflugrath et al. ............. 600/459 |
| 6,669,638 | B1 | | 12/2003 | Miller et al. |
| 6,705,995 | B1 | * | 3/2004 | Poland et al. ................ 600/447 |
| 6,709,398 | B2 | | 3/2004 | Umeda et al. |
| 6,869,400 | B2 | * | 3/2005 | Miyaki ......................... 600/437 |
| 8,052,606 | B2 | * | 11/2011 | Barnes et al. ................ 600/443 |
| 2002/0138007 | A1 | | 9/2002 | Nguyen-Dinh et al. |
| 2007/0167811 | A1 | | 7/2007 | Lemmerhirt et al. |
| 2008/0090199 | A1 | * | 4/2008 | Noguchi et al. ............... 433/29 |
| 2008/0097201 | A1 | | 4/2008 | Savord |
| 2010/0191120 | A1 | | 7/2010 | Kraus et al. |
| 2011/0137177 | A1 | * | 6/2011 | Toma et al. ................... 600/473 |
| 2011/0178405 | A1 | * | 7/2011 | Chono .......................... 600/443 |

FOREIGN PATENT DOCUMENTS

| JP | 05-0415074 U | 6/1993 |
| JP | 08-224206 A | 9/1996 |
| JP | 2002-526143 A | 8/2002 |
| JP | 2003-164450 A | 6/2003 |
| JP | 2004-350744 A | 12/2004 |
| JP | 2008-504057 A | 2/2008 |

(Continued)

*Primary Examiner* — Sanjay Cattungal
(74) *Attorney, Agent, or Firm* — Global IP Counselors, LLP

(57) ABSTRACT

A living body testing probe includes a living body contact part, a grip part, a non-mechanical switch part and a notification part. The living body contact part is configured and arranged to contact a living body. The non-mechanical switch part is configured and arranged to receive an operation input for changing test conditions upon being touched or approached. The notification part is configured and arranged to output information indicative of a change in the test conditions based on the operation input received by the non-mechanical switch part.

15 Claims, 4 Drawing Sheets

(56) References Cited

FOREIGN PATENT DOCUMENTS

| JP | 2010-172700 A | 8/2010 |
| JP | 2011-072467 A | 4/2011 |
| WO | 00/19905 A1 | 4/2000 |
| WO | 03/071919 A2 | 9/2009 |
| WO | 2011/150358 A1 | 12/2011 |

* cited by examiner

LIVING BODY TESTING PROBE

CROSS-REFERENCE TO RELATED APPLICATIONS

This application claims priority to Japanese Patent Application No. 2011-272131 filed on Dec. 13, 2011. The entire disclosure of Japanese Patent Application No. 2011-272131 is hereby incorporated herein by reference.

BACKGROUND

1. Technical Field

The present invention relates to a living body testing probe that conducts a test by contacting a living body.

2. Related Art

As a living body testing probe for testing the inside of a living body, there are an ultrasonic probe in which a test is conducted by using reflection of ultrasonic waves inside a living body, a probe for testing a pulse wave in which a test of a pulse wave is conducted by using reflection of infrared light inside a living body, and the like. Among these living body testing probes, for example, in the ultrasonic probe, an ultrasonic element, an ultrasonic lens section, or the like is disposed in a living body contact part of the probe main body, and the test conditions in the ultrasonic probe are changed in a main testing device connected to the ultrasonic probe with a wire or wirelessly. For example, conventional living body testing probes are disclosed in Japanese Laid-Open Patent Publication No. 2011-72467 and Japanese Laid-Open Patent Publication No. 2003-164450.

SUMMARY

The conventional living body testing probes described in the above mentioned publications, however, have a disadvantage that the main testing device needs to be operated with one hand to change the test conditions while operating the living body testing probe with the other hand. Accordingly, if a dial switch, a lever switch, or the like for changing the test conditions is provided in the living body testing probe itself, the usability will be improved. However, since the living body testing probe needs to be cleaned frequently due to its nature, providing a mechanical switch such as a dial switch or a lever switch for changing the test conditions causes a problem that a space or opening created in a movable portion of the mechanical switch is difficult to clean, and water and the like used for cleaning enters the inside of the living body testing probe from the space or opening in the movable portion to the mechanical switch, which easily results in occurrence of a defect.

In terms of the above-described circumstances, an object of the present invention is to provide a living body testing probe suitable for cleaning in which the test conditions are easily changed.

In order to achieve the above-described object, a living body testing probe according to one aspect of the present invention includes a living body contact part, a grip part, a non-mechanical switch part and a notification part. The living body contact part is configured and arranged to contact a living body. The non-mechanical switch part is configured and arranged to receive an operation input for changing test conditions upon being touched or approached. The notification part is configured and arranged to output information indicative of a change in the test conditions based on the operation input received by the non-mechanical switch part.

According to the above described aspect of the present invention, since the non-mechanical switch part is provided in the living body testing probe itself, changing the test conditions can easily be conducted in the living body testing probe. Further, since the non-mechanical switch that receives operation input for changing test conditions upon being touched or approached is used as the switch, opening and the like will not be easily formed unlike in the case of using a mechanical switch. Therefore, a portion difficult to clean will not easily occur, and a situation in which water and the like used for cleaning enters the inside of the living body testing probe from the space can be avoided. Consequently, a living body testing probe suitable for cleaning in which the test conditions are easily changed can be achieved.

The living body testing probe preferably further includes a display part configured and arranged to display at least the test conditions. With this configuration, the usability of the living body testing probe is improved because the operation for changing the test conditions and confirmation of the test conditions can be conducted in the living body testing probe.

In the living body testing probe, the display part preferably serves as the non-mechanical switch part. Specifically, by using the display part as a touch panel (non-mechanical switch), the size of the living body testing probe can be reduced compared to a case in which the switch is provided separately from the display part.

In the living body testing probe, the notification part preferably includes a signal output section configured and arranged to output an operation signal via a wire. With this configuration, the living body testing probe may be connected to a main testing device via the wire, and the test conditions may be changed in the main testing device. Accordingly, since the living body testing probe does not need to have a drive circuit and the like necessary for driving in the living body testing probe, the size of the living body testing probe can be reduced.

In the living body testing probe, the non-mechanical switch part is preferably an optical switch. With this configuration, liquid-tight properties of the switch can easily be achieved.

The optical switch is preferably an infrared switch configured and arranged to be operated by light emission and light reception of infrared light. This configuration has an advantage that outside light will not easily affect an operation with the switch.

In the living body testing probe, the non-mechanical switch part is preferably provided in a protruded area protruding with respect to a region surrounding the non-mechanical switch part, or in a recessed area recessed with respect to the region surrounding the non-mechanical switch part. With this configuration, the position of the non-mechanical switch can easily be sensed by touch.

The living body testing probe according to the above described aspect of the present invention may be configured as an ultrasonic probe, for example. In such a case, the living body contact part is configured and arranged to generate and receive ultrasonic waves, for example. In the case of the ultrasonic probe, since the living body contact part is caused to contact a surface of a living body with application of gel, the ultrasonic probe is frequently cleaned. Therefore, the effect of the present invention configured to be suitable for cleaning becomes significant.

BRIEF DESCRIPTION OF THE DRAWINGS

Referring now to the attached drawings which form a part of this original disclosure.

DETAILED DESCRIPTION OF EXEMPLARY EMBODIMENTS

Next, embodiments of the present invention will be explained in detail with reference to the attached drawings. In the following explanations, an ultrasonic probe that tests (examines) a state inside a living body with ultrasonic waves will be described as an example of a living body testing probe.

First Embodiment

Overall Configuration

Figure 1:
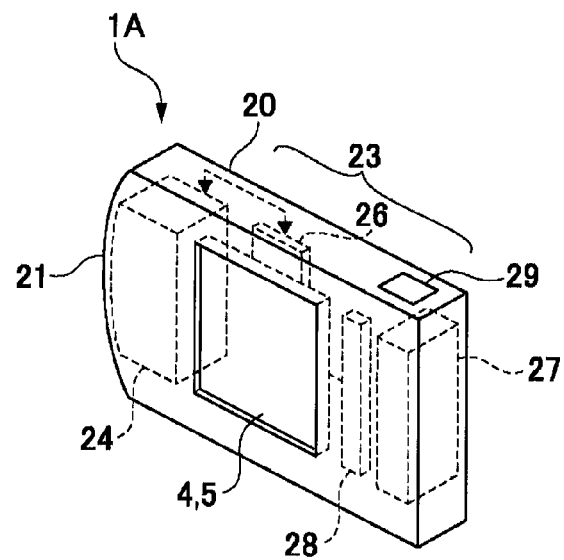
FIG. 1 is a simplified perspective view of an ultrasonic probe according to a first embodiment of the present invention.

FIG. 1 is a simplified perspective view of an ultrasonic probe 1A according to a first embodiment of the present invention. In the ultrasonic probe 1A shown in FIG. 1, a probe main body 20 has a generally flattened shape. The probe main body 20 has a living body contact part 21 for contacting the living body at the tip end thereof, and the rest of the probe main body 20 is used as a grip part 23. The tip end of the living body contact part 21 is curved in an arc shape as shown in FIG. 1. An ultrasonic transducer 24, an acoustic lens (not shown in the drawings), and the like are embedded in the living body contact part 21. The ultrasonic transducer 24 is provided with a plurality of elements configured such that an electrode is formed on both surfaces of a thick film of a piezoelectric body such as PZT (piezoelectric zirconate titanate) or polyvinylidene fluoride. When exciting pulses are applied to both the electrodes of this element, the piezoelectric body is caused to oscillate and generate ultrasonic waves, so that the inside of the living body is irradiated with the ultrasonic waves. When the ultrasonic transducer 24 receives reflected waves from the inside of the living body, the piezoelectric body is caused to oscillate and generate an electric signal, and this electric signal is converted into an ultrasound image.

In the present embodiment, a drive part 26 and a power supply part 27 are provided in the inside of the probe main body 20. A monitor 4 (one example of a display part) constructed of a liquid crystal display device is provided in the grip part 23 in a completely liquid-tight state. The drive part 26 drives the ultrasonic transducer 24. The drive part 26 also converts an electrical signal obtained via the ultrasonic transducer 24 into an ultrasound image (ultrasound image), and outputs it to the monitor 4. The ultrasound image obtained by the ultrasonic probe 1A is, therefore, displayed on the monitor 4. In the present embodiment, the monitor 4 is provided in a recessed region that is recessed slightly with respect to the surrounding regions in the outer circumferential surface of the probe main body 20.

In the ultrasonic probe 1A with the above-described configuration, a power supply switch 29 is provided on a side surface of the probe main body 20. The power supply switch 29 is a non-mechanical switch that uses a piezoelectric element, and is configured in a completely liquid-tight state.

Further, the ultrasonic probe 1A has a switch 5 (one example of a non-mechanical switch part) for changing test conditions provided in the probe main body 20. The ultrasonic probe 1A also has a notification part 28 that outputs information indicative of a change in the test conditions to the drive part 26 based on an operation in the switch 5. Examples of the test conditions include the intensity of ultrasonic waves, the scan mode (e.g., size of the scanning region, transmission frequency, focus depth, switching between different image modes such as B-mode and Doppler mode), and the like.

In the present embodiment, the switch 5 is a non-mechanical switch constructed of a resistive touch panel, a capacitance touch panel, or an optical touch panel, that is formed integrally with the monitor 4. The resistive touch panel, the capacitance touch panel, and the optical touch panel are conventional components that are well known in the art. Since these non-mechanical switches are well known in the art, these structures will not be discussed or illustrated in detail herein. Rather, it will be apparent to those skilled in the art from this disclosure that the components can be any type of structure and/or programming that can be used to carry out the present invention.

A menu switching button for switching the display into the settings of the test conditions is displayed on the monitor 4 as well as the ultrasound image obtained by the ultrasonic probe 1A. When a fingertip contacts or approaches the menu switching button, test condition selecting buttons are displayed. When a fingertip contacts or approaches a certain button among the test condition selecting buttons, the notification part 28 converts the results of selecting operation of the test conditions into a signal, and sends the signal to the drive part 26. As a result, the drive part 26 controls operation of the ultrasonic transducer, such as the output of ultrasonic waves from the ultrasonic transducer 24, according to the change in the test conditions. Accordingly, the optimum test conditions can be achieved depending on which part of the inside of a living body is tested. After the test conditions are changed in this manner, when a fingertip contacts or approaches the menu switching button, the display on the monitor 4 is switched into the display of an ultrasound image.

Effects of Present Embodiment

As explained above, in the ultrasonic probe 1A of the present embodiment, since the living body testing probe itself has the switch 5, the test conditions can easily be changed in the ultrasonic probe 1A. Also, since a touch panel (non-mechanical switch) in which an operation for changing test conditions is conducted by contact or proximity is used as the switch 5, a space and the like will not easily occur unlike in the case of using a mechanical switch that has a movable section. Therefore, a portion difficult to clean will not easily occur, and a situation in which water and the like used for cleaning enters the inside of the ultrasonic probe 1A from the space can be avoided. Consequently, the present embodiment can achieve the ultrasonic probe 1A suitable for cleaning in which the test conditions are easily changed.

In the ultrasonic probe 1A of the present embodiment, the monitor 4 that displays at least the test conditions is provided. Consequently, the usability of the ultrasonic probe 1A is improved because the operation for changing the test conditions and confirmation of the test conditions can be conducted in the ultrasonic probe 1A.

Further, since the monitor 4 also serves as the non-mechanical switch 5 for changing test conditions, the size of the ultrasonic probe 1A can be reduced compared to a case in which the switch 5 is provided separately from the monitor 4.

Further, the monitor 4 (switch 5) is configured to be in a recessed region that is recessed slightly with respect to the surrounding regions in the outer circumferential surface of the probe main body 20. Therefore, the position of the switch 5 can easily be sensed by touch.

In particular, in the case of the ultrasonic probe 1A among living body testing probes, since the living body contact part 21 is caused to contact a surface of a living body with application of gel, the ultrasonic probe 1A is frequently cleaned. Therefore, the effect of the ultrasonic probe 1A according to the present embodiment configured to be suitable for cleaning becomes significant.

Second Embodiment

Referring now to FIGS. 2 to 5, a living body testing probe in accordance with a second embodiment will now be explained. Since the basic configuration of the present embodiment is similar to that of the first embodiment, the components of the present embodiment that are identical or similar to the components of the first embodiment are indicated with a single prime ('). Moreover, in view of the similarity between the first and second embodiments, the descriptions of the parts of the second embodiment that are similar to the parts of the first embodiment may be omitted for the sake of brevity.

Overall Configuration

Figure 2:
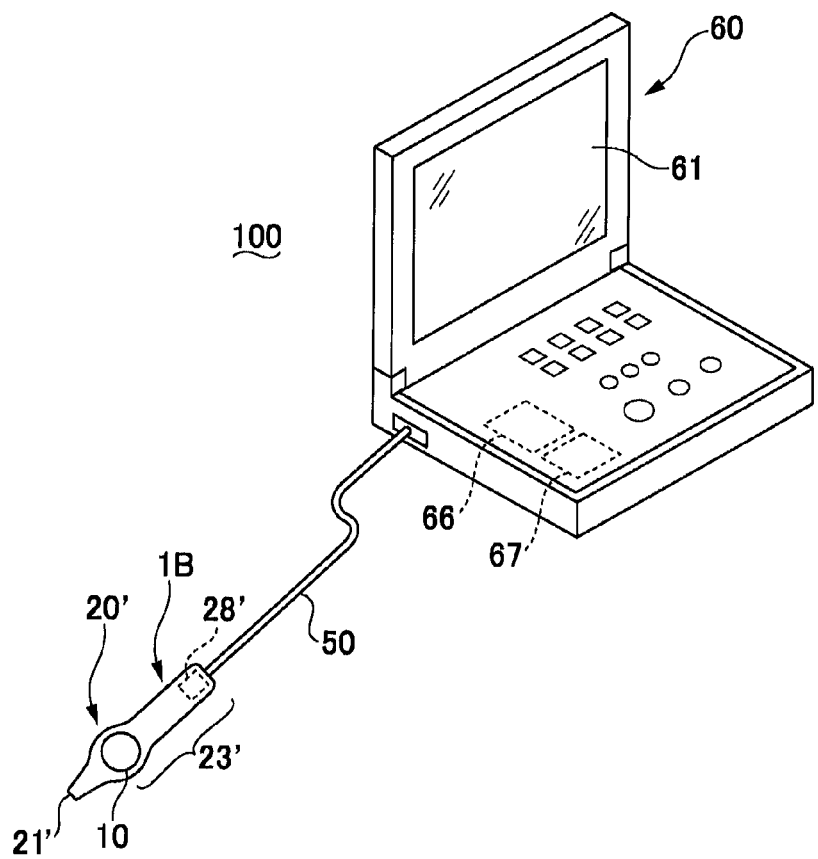
FIG. 2 is a simplified perspective view of a testing device provided with an ultrasonic probe according to a second embodiment of the present invention.
Figure 3A:
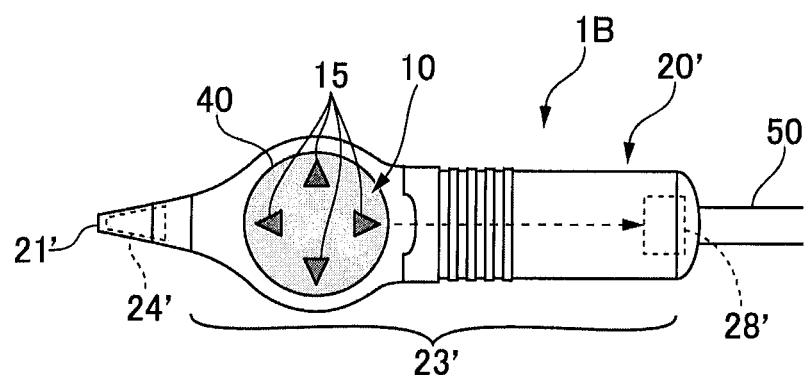
FIGS. 3A and 3B are simplified top plan view and side elevational view the ultrasonic probe according to the second embodiment of the present invention.
Figure 3B:
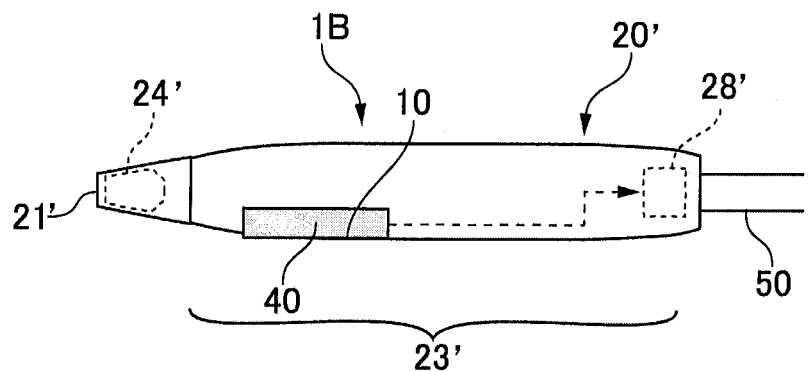

FIG. 2 is a simplified perspective view of a testing device provided with an ultrasonic probe 1B according to a second embodiment of the present invention. FIGS. 3A and 3B are enlarged views of the ultrasonic probe 1B according to the second embodiment of the present invention. Specifically, FIG. 3A is a top plan view of the ultrasonic probe 1B, and FIG. 3b is a side view of the ultrasonic probe 1B.

In the first embodiment explained above, the drive circuit 26 and the monitor 4 are provided in the ultrasonic probe 1A itself. In the present embodiment, however, an ultrasonic probe 1B is connected to a main testing device 60 provided with a monitor 61 and the like via a cable 50, as shown in a testing device 100 of FIG. 2. The main testing device 60 is also provided with a drive part 66 and a power supply part 67 for the ultrasonic probe 1B as well as the monitor 61. Power feeding to the ultrasonic probe 1B and driving the ultrasonic probe 1B are conducted from the main testing device 60 by the cable 50. Also, an electrical signal obtained in the ultrasonic probe 1B is output to the main testing device 60 via the cable 50, and an ultrasound image is displayed on the monitor 61 of the main testing device 60.

In the present embodiment, similarly to the first embodiment, the ultrasonic probe 1B has a switch 10 for easily changing test conditions, and the ultrasonic probe 1B also has the notification part 28' that output information indicative of a change in the test conditions based on an operation to the switch 10.

More specifically, as shown in FIGS. 3A and 3B, in the ultrasonic probe 1B of the present embodiment, the probe main body 20' has a generally rod shape as a whole, and the probe main body 20' has the living body contact part 21' at the tip end thereof. The rest of the probe main body 20' other than the living body contact part 21' is used as the grip part 23'. The living body contact part 21' is configured to be in a bulging area that bulges in a hemispherical shape as shown in FIG. 3A, and the ultrasonic transducer 24', an acoustic lens (not shown in the drawings), and the like are embedded in the inside of the living body contact part 21'.

In the probe main body 20', the switch 10 for changing test conditions such as the intensity of ultrasonic waves is provided in the grip part 23', and the notification part 28' that outputs information indicative of a change in the test conditions based on an operation in the switch 10 to the drive part 66 of the main testing device 60 by the cable 50 is provided in an end portion of the grip part 23' on the opposite side of the living body contact part 21'. In the present embodiment, the notification part 28' is a signal output section that outputs an operation signal in the switch 10 to the main testing device 60 via the cable 50 (one example of a wire). The notification part 28' also has a function of sending an electrical signal obtained in the ultrasonic transducer 24' to the drive part 66 of the main testing device 60 by the cable 50.

Here, the switch 10 is an optical switch for changing test conditions based on a contact position or a proximity position of a fingertip, and such an optical switch is a type of a non-mechanical switch that does not have a movable portion. Various kinds of conventional non-mechanical switches can be used as the switch 10. In the present embodiment, for example, the optical position detection device disclosed in Japanese Laid-open Patent Publication No. 2011-232191 and the like can be used.

Configuration of Switch 10

Figure 4A:
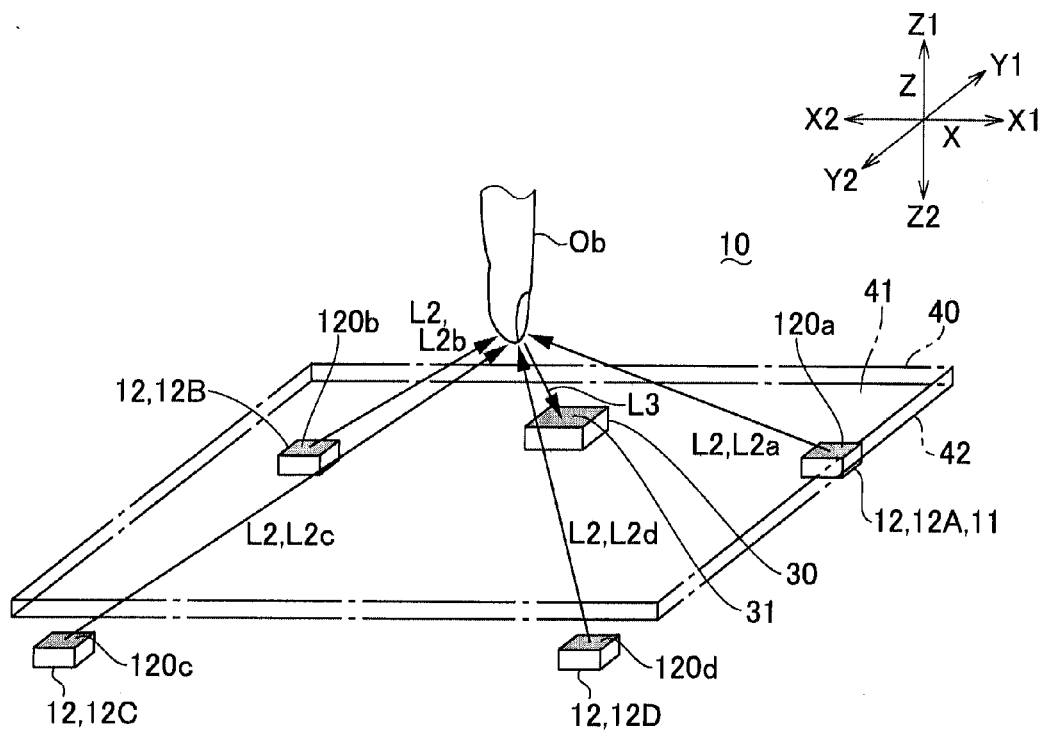
FIGS. 4A and 4B are explanatory diagrams of an optical position detection device used as a switch in the ultrasonic probe according to the second embodiment of the present invention.
Figure 4B:
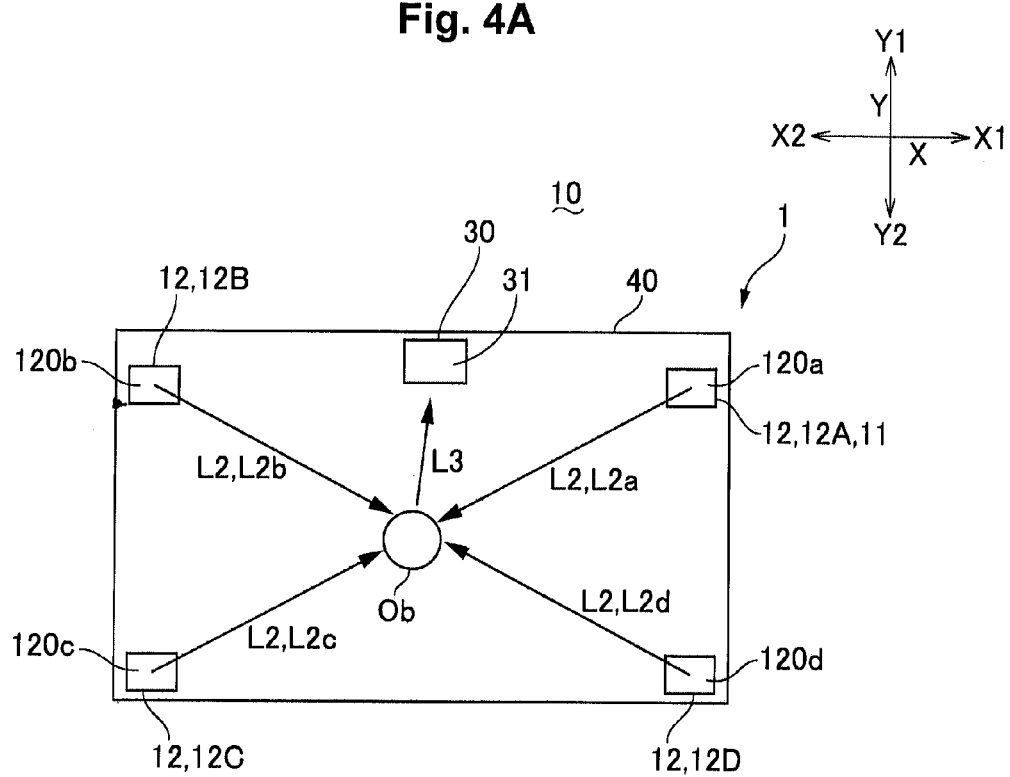

FIGS. 4A and 4B are explanatory diagrams of an optical position detection device used as the switch 10 in the ultrasonic probe 1B according to the second embodiment of the present invention. Specifically, FIG. 4A is an explanatory diagram showing an overall configuration of the optical position detection device, and FIG. 4B is an explanatory diagram showing a positional relationship of a light source section and the like.

As shown in FIGS. 4A and 4B, the optical position detection device used as the switch 10 in the ultrasonic probe 1B of the present embodiment has a translucent member 40, a light source device 11, a light receiving section 30, and the like. More specifically, the light source device 11 of the switch 10 has a plurality of light source sections 12 that emit detection light L2 toward a side Z1 of a Z axis direction, and the light receiving section 30 of the switch 10 detects detection light L3 reflected on a target object Ob such as a fingertip. In the switch 10, the light source sections 12 emit the detection light L2 from a rear surface 42 side of the translucent member 40 to a front surface 41 side of the translucent member 40, and the light receiving section 30 detects the detection light L3 reflected on the target object Ob and transmitted toward the rear surface 42 side of the translucent member 40. For this purpose, a light receiving surface 31 of the light receiving section 30 faces the rear surface 42 of the translucent member 40.

The light source device 11 has a first light source section 12A, a second light source section 12B, a third light source section 12C, and a fourth light source section 12D as the plurality of light source sections 12 on the rear surface 42 side of the translucent member 40. These light source sections 12 have light emitting sections 120a-120d directed toward the translucent member 40, respectively. The detection light L2 (detection light L2a-L2d) emitted from the light source sections 12 is transmitted through the translucent member 40 and exits toward the visible front surface 41 side (detection light exit space of the detection light L2 from the light source device 11). In the present embodiment, this detection light exit space (space on the visible front surface 41 side) forms a detection space in which the position of the target object Ob is detected.

The first light source section 12A, the second light source section 12B, the third light source section 12C, and the fourth light source section 12D are arranged in positions that correspond to corners of a rectangle respectively when seen from the detection space (Z axis direction). Each of the light source sections 12 (the first light source section 12A, the second light source section 12B, the third light source section 12C, and the fourth light source section 12D) is constructed of a light emitting element such as an LED (light emitting diode). In the present embodiment, each of the light source sections 12 emits the detection light L2 (detection light L2a-L2d) composed of infrared light whose peak wavelength is located in 840-1000 nm as diverging light. In the present embodiment, since the target object Ob is often a fingertip, infrared light (near infrared light of around 840-920 nm) having a wavelength range in which reflectivity with respect to the target object Ob (human body) is high is used as the detection light L2.

The light receiving section 30 is a photo diode, a photo transistor, or the like, in which the light receiving surface 31 faces the translucent member 40. In the present embodiment, the light receiving section 30 is a photo diode that has a sensitivity peak in an infrared region.

In the switch 10, the position of the target object Ob (fingertip) in the detection space is detected based on the light receiving results in the light receiving section 30 when the plurality of the light source sections 12 are sequentially lighted up. For example, based on the light receiving results in the light receiving section 30 when two of the light source sections 12 spaced apart in an X direction are sequentially lighted up, the ratio of the distance between one of the two light source sections 12 and the target object Ob and the distance between the other of the two light source sections 12 and the target object Ob is obtained. Also, based on the light receiving results in the light receiving section 30 when two of the light source sections 12 spaced apart in a Y direction are sequentially lighted up, the ratio of the distance between one of the two light source sections 12 and the target object Ob and the distance between the other of the two light source sections 12 and the target object Ob is obtained. Then, the X-Y coordinate position of the target object Ob is detected by combining the above results. Further, if a temporal change in the position of the target object Ob is detected, the movement of the target object Ob (movement of fingertip) as shown by arrows 15 of FIG. 3A can be detected. In the present embodiment, therefore, the position or movement of the target object Ob is related to the test conditions, and the test conditions are changed depending on a position of a fingertip in the switch 10 or depending on a movement direction of a fingertip.

In a case where the light receiving intensity in the light receiving section 30 is equal to or less than a predetermined value, it may be configured to determine that there is no operation for changing test conditions because a fingertip is away from the switch 10. Consequently, an erroneous operation can be prevented.

Effects of Present Embodiment

As explained above, similarly to the above-described first embodiment, the ultrasonic probe 1B of the present embodiment has the switch 10 provided in the living body testing probe itself. Thus, the test conditions can easily be changed in the ultrasonic probe 1B. Also, since an optical position detection device (non-mechanical switch) in which an operation for changing test conditions is conducted by contact or proximity is used as the switch 10, a space or opening will not easily formed in the ultrasonic probe 1B unlike in the case of using a mechanical switch that has a movable section. Therefore, a portion difficult to clean will not easily occur, and a situation in which water and the like used for cleaning enters the inside of the ultrasonic probe 1B from the space can be avoided. Consequently, the present embodiment has a similar effect as the first embodiment, and the ultrasonic probe 1B suitable for cleaning in which the test conditions are easily changed can be achieved, for example.

In the present invention, since the notification part 28' is a signal output section that outputs an operation signal via the cable 50, the test conditions can be changed from the main testing device 60 by the cable 50. Accordingly, since the ultrasonic probe 1B does not need to have a circuit and the like necessary for driving in the ultrasonic probe 1B, the size of the ultrasonic probe 1B can be reduced.

Further, since the switch 10 is an optical switch, liquid-tight properties of the switch 10 can easily be achieved. Furthermore, since the optical switch 10 is an infrared switch that uses light emission and light reception of infrared light, it has an advantage that outside light will not easily affect an operation with the switch 10.

Modification Example of Second Embodiment

Figure 5:
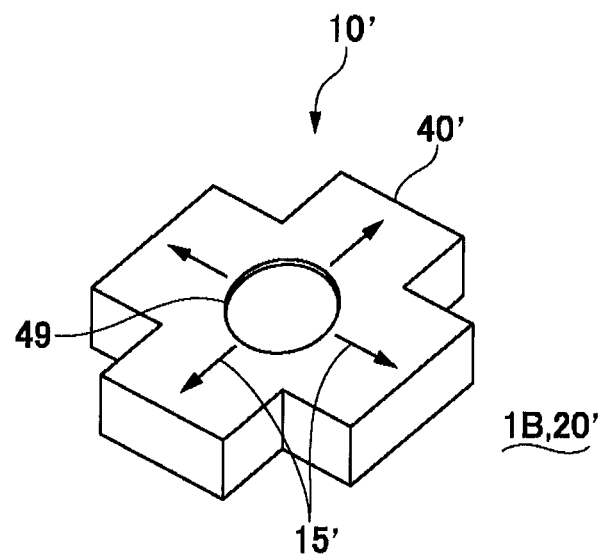
FIG. 5 is a simplified perspective view of a switch provided in the ultrasonic probe according to a modification example of the second embodiment of the present invention.

FIG. 5 is an explanatory diagram of the switch 10' provided in the ultrasonic probe 1B according to a modification example of the second embodiment of the present invention.

The switch 10 explained in the second embodiment may be configured to be in the same plane as an outer circumferential surface of the probe main body 20. In this modification example, the switch 10' is configured such that the translucent member 40' is protruded with respect to the outer circumferential surface of the probe main body 20' as shown in FIG. 5. With this configuration, since the switch 10' can be configured to be a protruded section, the position of the switch 10' can easily be sensed by touch.

When the planar view shape of the translucent member 40' is a cross shape protruded in an operation direction as shown by arrows 15', it has an advantage that the operation direction can be sensed by touch. Further, a shallow recessed section 49 may be formed in the center of the translucent member 40' such that the recessed section 49 indicates a reference position.

Alternatively, the translucent member 40 may be formed to be recessed with respect to the outer circumferential surface of the probe main body 20. With this configuration, since the switch 10 can be configured to be a recessed region, the position of the switch 10 can easily be sensed by touch.

Third Embodiment

Figure 6:
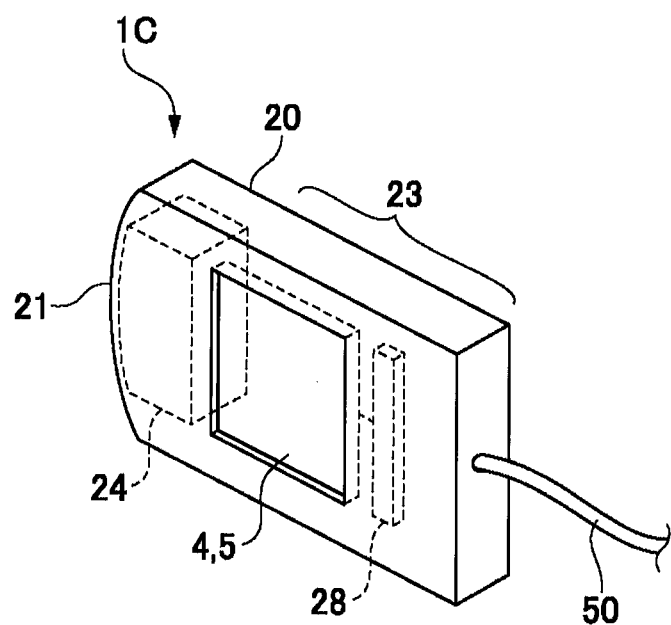
FIG. 6 is a simplified perspective view of an ultrasonic probe according to a third embodiment of the present invention.

Referring now to FIG. 6, a living body testing probe in accordance with a third embodiment will now be explained. Since the basic configuration of the present embodiment is similar to that of the first or second embodiment, the components of the present embodiment that are identical or similar to the components of the first or second embodiment will be given the same reference numerals as the parts of the first or second embodiment. Moreover, in view of the similarity between the first, second and third embodiments, the descriptions of the parts of the third embodiment that are similar to the parts of the first or second embodiment may be omitted for the sake of brevity.

FIG. 6 is a simplified perspective view of an ultrasonic probe according to a third embodiment of the present invention.

In the second embodiment, the monitor 4 is not provided in the ultrasonic probe 1B that is connected to the main testing device 60 by the cable 50. In the present embodiment, however, as shown in FIG. 6, an ultrasonic probe 1C provided with the monitor 4 is connected to the main testing device 60 via the cable 50. The other configurations are substantially similar to the first embodiment.

Unlike the first embodiment, the ultrasonic probe 1C does not have the drive part 26 and the power supply part 67. Therefore, the monitor 4 displays the test conditions as the monitor 4 is mainly used as the switch 5 (touch panel).

Other Embodiment

In the first embodiment, the ultrasonic probe 1A itself serves as the testing device. In a case where it is difficult to see test results with the small monitor 4, however, it may be configured such that test results obtained by the ultrasonic probe 1A are output to the main testing device 60 shown in FIG. 2 with a wire or wirelessly.

Although an ultrasonic probe is described as an example of the living body testing probe in the above described first to third embodiments, the present invention can be applied to other types of a testing probe such as a probe for testing a pulse wave in which a test of a pulse wave is conducted by using reflection of infrared light inside a living body.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A living body testing probe comprising:
   a probe main body having a living body contact part that is disposed on an end portion of the probe main body and is configured to contact a living body, and a grip part that is disposed on a middle portion of the probe main body and is configured to be held by a user's hand while the living body contact part contacts the living body;
   a display part disposed in a recessed area of a surface of the grip part and configured to display a test condition;
   a non-contact switch part integrated with the display part and configured to receive an operation input for changing the test condition upon being approached; and
   a notification part disposed within the grip part and configured to output information of the test condition based on the operation input received by the non-contact switch part,
   the display part and the non-contact switch part being at least partially located at a location closer to the end portion of the probe main body relative to a lengthwise center of the probe main body, and
   the living body contact part being configured to generate and receive ultrasonic waves.

2. The living body testing probe according to claim 1, wherein
   the display part serves as the non-contact switch part.

3. The living body testing probe according to claim 1, wherein
   the notification part includes a signal output section configured to output an operation signal via a wire.

4. The living body testing probe according to claim 1, wherein
   the non-contact switch part is an optical switch.

5. The living body testing probe according to claim 4, wherein
   the optical switch is an infrared switch configured to be operated by light emission and light reception of infrared light.

6. The living body testing probe according to claim 4, wherein
   the optical switch has a translucent member, a plurality of light source sections and a light receiving section.

7. The living body testing probe according to claim 1, wherein
   the non-contact switch part is provided in the recessed area recessed with respect to the region surrounding the non-contact switch part.

8. The living body testing probe according to claim 7, wherein
   the non-contact switch part is an optical switch, and
   the optical switch and the display part are provided in the recessed area.

9. The living body testing probe according to claim 1, wherein
the display part has an outer surface that is inwardly recessed relative to the surface of the grip part.

10. A living body testing probe comprising:
a main body;
a living body contact part disposed on an end portion of the main body and configured to contact a living body;
a grip part disposed on a middle portion of the main body and configured to be held by a user's hand while the living body contact part contacts the living body;
a display part disposed in a recessed area of a surface of the grip part and configured to display a test condition;
a non-contact switch part integrated with the display part and configured to receive an operation input for changing the test condition upon being approached, the non-contact switch part including an optical switch that has a translucent member, a plurality of light source sections and a light receiving section; and
a notification part disposed within the grip part and configured to output information of the test condition based on the operation input received by the non-contact switch part,
the display part and the non-contact switch part being at least partially located at a location closer to the end portion of the main body relative to a lengthwise center of the main body.

11. The living body testing probe according to claim 10, wherein
the light source sections are configured to emit infrared light, and
the light receiving section is configured to receive the infrared light.

12. The living body testing probe according to claim 10, wherein
the non-contact switch part is configured to detect a position of a target object for the operation input based on light reception result of the light receiving section in response to sequential light emission of the light source sections.

13. The living body testing probe according to claim 10, wherein
the non-contact switch part is disposed on the grip part.

14. An indicating instrument comprising:
a main body with a living body contact part disposed on an end portion of the main body and a grip part disposed on a middle portion of the main body;
a display part disposed in a recessed area of a surface of the grip part and configured to display a condition;
a non-contact switch part integrated with the display part and configured to receive an operation input for indicating the condition upon being approached; and
a notification part disposed within the grip part and configured to output information indicative of the condition based on the operation input received by the non-contact switch part,
the display part and the non-contact switch part being at least partially located at a location closer to the end portion of the main body relative to a lengthwise center of the main body, and
the living body contact part being configured to generate and receive ultrasonic waves.

15. An apparatus comprising:
a main body with a living body contact part disposed on an end portion of the main body and a grip part disposed on a middle portion of the main body;
a display part disposed in a recessed area of a surface of the grip part and configured to display information;
a non-contact switch part integrated with the display part and configured to receive an operation input upon being approached; and
a notification part disposed within the grip part and configured to output the information based on the operation input received by the non-contact switch part,
the display part and the non-contact switch part being at least partially located at a location closer to the end portion of the main body relative to a lengthwise center of the main body, and
the living body contact part being configured to generate and receive ultrasonic waves.

* * * * *